(12) United States Patent
Burgo et al.

(10) Patent No.: US 9,610,237 B2
(45) Date of Patent: Apr. 4, 2017

(54) NATURAL SILICONE REPLACEMENTS FOR SILICONE FLUIDS IN PERSONAL CARE FORMULATIONS

(71) Applicant: INOLEX INVESTMENT CORPORATION, Wilmington, DE (US)

(72) Inventors: Rocco Burgo, Mullica Hill, NJ (US); Daniel Winn, Kingston, NJ (US); Kimberly Burch, Trenton, NJ (US)

(73) Assignee: Inolex Investment Corporation, Wilmington, DE (US)

( * ) Notice: Subject to any disclaimer, the term of this patent is extended or adjusted under 35 U.S.C. 154(b) by 0 days.

(21) Appl. No.: 14/276,788

(22) Filed: May 13, 2014

(65) Prior Publication Data

US 2014/0356303 A1 Dec. 4, 2014

Related U.S. Application Data

(63) Continuation of application No. PCT/US2012/065052, filed on Nov. 14, 2012.

(Continued)

(51) Int. Cl.
*A61K 8/85* (2006.01)
*A61K 8/37* (2006.01)
(Continued)

(52) U.S. Cl.
CPC ............ *A61K 8/85* (2013.01); *A61K 8/37* (2013.01); *A61Q 1/04* (2013.01); *A61Q 5/12* (2013.01); *A61Q 19/00* (2013.01); *A61K 2800/34* (2013.01)

(58) Field of Classification Search
CPC ......... A61K 2800/34; A61K 8/37; A61K 8/85
See application file for complete search history.

(56) References Cited

U.S. PATENT DOCUMENTS 4,366,100 A * 12/1982 Naskar ............... A61K 8/375
554/164
4,988,463 A * 1/1991 Walz ................ B01D 19/0404
516/131

(Continued)

FOREIGN PATENT DOCUMENTS

JP 2000-212049 A 8/2000
JP 2004-262783 A 9/2004

(Continued)

OTHER PUBLICATIONS

International Search Report and Written Opinion dated Mar. 12, 2013 (8 pages).

(Continued)

*Primary Examiner* — Aradhana Sasan
(74) *Attorney, Agent, or Firm* — Flaster/Greenberg P.C.

(57) ABSTRACT

Described herein is a silicone replacement for use in a personal care formulation comprising a mixture of at least one polymeric ester and at least one non-polymeric ester. The polymeric ester is an esterification reaction product of (i) at least one first dicarboxylic acid, (ii) at least one first monofunctional alcohol or monofunctional carboxylic acid and (iii) glycerin or derivatives thereof. The non-polymeric ester is an esterification reaction product of (i) at least one second dicarboxylic acid and (ii) at least one second monofunctional alcohol, wherein the replacement is substantially free of silicone. As described is a personal care formulation that is substantially free of silicone, wherein the formulation comprises a silicone replacement consisting substantially of a mixture of at least one polymeric ester as described above, and a non-polymeric ester as described above. Related methods are also described.

14 Claims, 16 Drawing Sheets

Related U.S. Application Data

(60) Provisional application No. 61/559,266, filed on Nov. 14, 2011.

(51) Int. Cl.
    *A61Q 19/00*     (2006.01)
    *A61Q 1/04*     (2006.01)
    *A61Q 5/12*     (2006.01)

(56) References Cited

U.S. PATENT DOCUMENTS

| | | |
|---|---|---|
| 2001/0006652 A1 | 7/2001 | Kahre et al. |
| 2004/0241200 A1 | 12/2004 | Winn et al. |
| 2004/0258642 A1 | 12/2004 | Calello et al. |
| 2005/0260150 A1* | 11/2005 | Burgo .............. A61K 8/375 |
| | | 424/70.11 |
| 2005/0288478 A1 | 12/2005 | Burgo |
| 2008/0051470 A1 | 2/2008 | Issberner et al. |
| 2009/0123398 A1 | 5/2009 | Laba et al. |
| 2010/0068162 A1 | 3/2010 | Greenberg et al. |
| 2011/0020258 A1 | 1/2011 | Lorant |
| 2011/0064685 A1 | 3/2011 | Jordan |

FOREIGN PATENT DOCUMENTS

| | | |
|---|---|---|
| JP | 2011-506556 A | 3/2011 |
| WO | 2005/097044 A1 | 10/2005 |
| WO | 2010/019939 A1 | 2/2010 |

OTHER PUBLICATIONS

Supplementary European Search Report dated Apr. 17, 2015 (9 page).
First Swiss Office Action dated Sep. 30, 2014 (2 pages).
Response to First Swiss Office Action dated Dec. 24, 2014 (14 pages).
Second Swiss Office Action dated Feb. 27, 2015 (2 pages).
Response to Second Swiss Office Action dated May 26, 2015 (1 page).
Third Swiss Office Action dated Sep. 30, 2015 (2 pages).
Response to Third Swiss Office Action dated Apr. 6, 2016 (14 pages).
Freeman Organic Chemistry, "Carboxylic Products in Nature" pp. 133-134 (3 pages).
Japanese Office Action dated Nov. 1, 2016 in Application No. 2014-541417 (counterpart of U.S. Appl. No. 14/276,788) (10 pages).

* cited by examiner

FIGURE 4

| INGREDIENTS | | 582-177A %w/w | 582-177B %w/w | 582-177C %w/w | 582-177D %w/w | 582-177E %w/w | 586-093F %w/w | 586-093G %w/w |
|---|---|---|---|---|---|---|---|---|
| A | Deionized Water | 76.15 | 76.15 | 76.15 | 76.15 | 76.15 | 76.15 | 76.15 |
| | Xanthan Gum Keltrol CG-T | 0.25 | 0.25 | 0.25 | 0.25 | 0.25 | 0.25 | 0.25 |
| | Microcrystalline Cellulose (and) Cellulose Gum Avicel PC611 | 1.00 | 1.00 | 1.00 | 1.00 | 1.00 | 1.00 | 1.00 |
| | Glycerin | 4.00 | 4.00 | 4.00 | 4.00 | 4.00 | 4.00 | 4.00 |
| | Trisodium EDTA | 0.10 | 0.10 | 0.10 | 0.10 | 0.10 | 0.10 | 0.10 |
| B | Glyceryl Stearate SE Lexemul T | 5.00 | 5.00 | 5.00 | 5.00 | 5.00 | 5.00 | 5.00 |
| | Ceryl Alcohol | 2.50 | 2.50 | 2.50 | 2.50 | 2.50 | 2.50 | 2.50 |
| | Dimethicone DC 200/10 | 10.00 | --- | --- | --- | --- | --- | --- |
| | N10 | --- | 10.00 | --- | --- | --- | --- | --- |
| | Dimethicone DC200/20 | --- | --- | 10.00 | --- | --- | --- | --- |
| | N20 | --- | --- | --- | 10.00 | --- | --- | --- |
| | Dimethicone DC200/100 | --- | --- | --- | --- | 10.00 | --- | --- |
| | LexFeel N100 | --- | --- | --- | --- | --- | 10.00 | --- |
| | Dimethicone DC200/200 | --- | --- | --- | --- | --- | --- | --- |
| | N200 | --- | --- | --- | --- | --- | --- | 10.00 |
| | Dimethicone DC200/350 | --- | --- | --- | --- | --- | --- | --- |
| | N350 | --- | --- | --- | --- | --- | --- | --- |
| C | Caprylhydroxamic Acid (and) Caprylyl Glycol (and) Glycerin Spectrastat™ | 1.00 | 1.00 | 1.00 | 1.00 | 1.00 | 1.00 | 1.00 |
| | Total | 100.00 | 100.00 | 100.00 | 100.00 | 100.00 | 100.00 | 100.00 |

FIGURE 4 (continued)

| INGREDIENTS | | 582-177A %w/w | 582-177B %w/w | 582-177C %w/w | 582-177D %w/w | 582-177E %w/w | 586-093F %w/w | 586-093G %w/w |
|---|---|---|---|---|---|---|---|---|
| A | Deionized Water | 76.15 | 76.15 | 76.15 | 76.15 | 76.15 | 76.15 | 76.15 |
| | Xanthan Gum Keltrol CG-T | 0.25 | 0.25 | 0.25 | 0.25 | 0.25 | 0.25 | 0.25 |
| | Microcrystalline Cellulose (and) Cellulose Gum Avicel PC611 | 1.00 | 1.00 | 1.00 | 1.00 | 1.00 | 1.00 | 1.00 |
| | Glycerin | 4.00 | 4.00 | 4.00 | 4.00 | 4.00 | 4.00 | 4.00 |
| | Trisodium EDTA | 0.10 | 0.10 | 0.10 | 0.10 | 0.10 | 0.10 | 0.10 |
| B | Glyceryl Stearate SE Lexemul T | 5.00 | 5.00 | 5.00 | 5.00 | 5.00 | 5.00 | 5.00 |
| | Cetyl Alcohol | 2.50 | 2.50 | 2.50 | 2.50 | 2.50 | 2.50 | 2.50 |
| | Dimethicone DC 200/10 N10 | 10.00 | --- | --- | --- | --- | --- | --- |
| | Dimethicone DC200/20 N20 | --- | 10.00 | --- | --- | --- | --- | --- |
| | Dimethicone DC200/100 N100 | --- | --- | 10.00 | --- | --- | --- | --- |
| | Dimethicone DC200/200 N200 | --- | --- | --- | 10.00 | --- | --- | --- |
| | Dimethicone DC200/350 N350 | --- | --- | --- | --- | 10.00 | --- | --- |
| | Dimethicone | --- | --- | --- | --- | --- | 10.00 | --- |
| | Dimethicone | --- | --- | --- | --- | --- | --- | 10.00 |
| C | Caprylhydroxamic Acid (and) Caprylyl Glycol (and) Glycerin Spectrastat™ | 1.00 | 1.00 | 1.00 | 1.00 | 1.00 | 1.00 | 1.00 |
| | Total | 100.00 | 100.00 | 100.00 | 100.00 | 100.00 | 100.00 | 100.00 |

FIGURE 5

SURVEY:

We are studying the attributes of a series of new natural emollients. Each participant will receive a set of two samples for evaluation twice a day for the next three days.
Please apply sample to forearm as directed and record evaluation of products below.

Name: _____

Product A: _____

Product B: _____

1. Product A a. How does lotion feel when applied?
   Light . . . . . . . . . . . . . . . . . . . . . . . . . . . . . . . Rich
     1        2        3        4        5 b. How does your skin feel during rub-in (mid-application)?
   Slippery . . . . . . . . . . . . . . . . . . . . . . . . . . . Sticky
     1        2        3        4        5 c. How long does it take for the product to be absorbed?
   Quick . . . . . . . . . . . . . . . . . . . . . . . . . . . . . Long
     1        2        3        4        5 d. How does your skin feel immediately after application? Is there a residue?
   Not Oily . . . . . . . . . . . . . . . . . . . . . . . . . . . Very Oily
     1        2        3        4        5 e. After 5 minutes, how does your skin feel?
   No Residual . . . . . . . . . . . . . . . . . . . . . . . . Rich Residual (waxy, greasy, silky, etc.)
     1        2        3        4        5

2. Repeat evaluation with product B

Record feedback:
   Product B a. How does lotion feel when applied?
   Light . . . . . . . . . . . . . . . . . . . . . . . . . . . . . . . Rich
     1        2        3        4        5 b. How does your skin feel during rub-in (mid-application)?
   Slippery . . . . . . . . . . . . . . . . . . . . . . . . . . . Sticky
     1        2        3        4        5 c. How long does it take for the product to be absorbed?
   Quick . . . . . . . . . . . . . . . . . . . . . . . . . . . . . Long
     1        2        3        4        5 d. How does your skin feel immediately after application? Is there a residue?
   Not Oily . . . . . . . . . . . . . . . . . . . . . . . . . . . Very Oily
     1        2        3        4        5 e. After 5 minutes, how does your skin feel?
   No Residual . . . . . . . . . . . . . . . . . . . . . . . . Rich Residual (waxy, greasy, silky, etc.)
     1        2        3        4        5

NATURAL SILICONE REPLACEMENTS FOR SILICONE FLUIDS IN PERSONAL CARE FORMULATIONS

CROSS-REFERENCE TO RELATED APPLICATIONS

This application is a continuation of International Application No. PCT/US2012/065052, filed Nov. 14, 2011, which in turn claims the benefit under 35 U.S.C. §119(e) to U.S. Provisional Patent Application No. 61/559,266, filed Nov. 14, 2011; the entire disclosures of each of which are incorporated herein by this reference.

BACKGROUND OF THE INVENTION

Silicone fluids are widely used in toiletry, cosmetic, and personal care formulations. Most frequently used are the dimethicones, the cyclomethicones, and phenyl trimethicone (hereinafter all silicone materials collectively refereed to as "silicones"). Incorporated into a skin care formulation, silicone fluids provide a variety of benefits such as improved slip, reduction of tack, impartation of emolliency, and other modifications of the "feel" characteristics of the formulation, as well as other benefits. Incorporated into hair care formulations such as conditioners, they can reduce wet combing force and increase shine of hair Silicone fluids have been considered to be particularly useful as they tend to provide the aforementioned benefits without contributing to oiliness or greasiness and give what many consider to be a "dry" skin feel. This attribute is highly desired in toiletry, cosmetic, and other personal care formulations such as creams, lotions, antiperspirants, shaving formulations, and make-up formulations. Additional benefits are that silicones are excellent dispersing and spreading agents, are generally water white in color, low in odor, and are resistant to chemical and oxidative attack. These attributes make them particularly suitable for personal care applications. However, the use of silicones in personal care formulation comes with drawbacks.

For example, there has been concern about the safety of the use of silicone fluids on the skin. In light of potential links between silicone and silicone degradation products to the development of autoimmune system deficiencies in women with silicone breast implants and/or individuals with other disorders, these materials have recently come under higher scrutiny by the Food and Drug Administration (FDA). Although definitive links have not been confirmed, many cosmetic formulators have acted to attempt to reduce and or eliminate silicone ingredients from formulations. The downside of not using silicones is of course that the skin feel and formulation benefits are lost.

In addition, silicones have also been implicated as potentially being harmful to the environment. For example, Environment Canada has published a documents indicating that dimethiciones are suspected to be environmental toxins and biocumulative.

Accordingly, there exists a need in the art to identify alternative non-silicone fluids that provide silicone-like benefits in formulation but do not bring with the real or perceived health and environmental risks.

The industry has made efforts to respond to this need. For example, U.S. Patent Application Publication 2005/0260150 describes low viscosity esters that may be used as replacements for low viscosity silicone fluids. United States Patent Application Publication 2004/0241200 describes blends of certain synthetic esters with volatile hydrocarbons that are useful for the replacement of volatile tetramer and pentamer cyclomethicones. United States Patent Application Publication 2009/0123398 describes blends of hydrocarbon fluids useful for the replacement of volatile tetramer and pentamer cyclomethicones. United States Patent Application Publication 2011/0064685 describes personal care compositions comprising an aqueous dispersion comprising a metallocene catalyzed polyolefin and an ethylene acrylic acid copolymer; a cationic polymer; and a least one cosmetically acceptable surfactant, emollient, or cosmetic active, provided that the personal care composition contains less than 0.09 wt % of 15 silicone, and preferably is substantially free of silicone.

As the population becomes more aware of the potential adverse effects to the body and to the environment associated with the use ingredients derived from fossil fuels, the personal care industry has rapidly advanced their search for "natural" ingredients for use in virtually all cosmetic formulation types and forms. Media has driven this growth by popularizing the idea that there may be potential adverse effects to the body and to the environment associated with the use ingredients derived from fossil fuels. The personal care industry has rapidly advanced its attempts to identify "natural" ingredients for use in virtually all cosmetic product types and forms. Notably, although used in marketing materials, the term "natural" has not yet been clearly defined within this context; efforts are under way by industry trade organizations to give the term a more concise and consistent meaning.

It may be some time before an industry accepted universal definition of natural is provided; however, it is generally recognized that materials derived from renewable and/or sustainable, or otherwise non-fossil fuel sources are considered to be natural. Petrochemicals are derived from fossil fuels and are not considered to be natural. Any derivatives of petrochemicals are not considered to be natural. As such, silicones are not classified as natural, as they are petrochemically derived. Accordingly, there is a need in the art for natural silicone replacements that can be used in lieu of silicones in personal care formulations and which provide to the consumer the advantageous end properties of silicones.

BRIEF SUMMARY OF THE INVENTION

Described herein is a silicone replacement for use in a personal care formulation comprising a mixture of at least one polymeric ester and at least one non-polymeric ester. The polymeric ester is an esterification reaction product of (i) at least one first dicarboxylic acid, (ii) at least one first monofunctional alcohol or monofunctional carboxylic acid and (iii) glycerin or derivatives thereof. The non-polymeric ester is an esterification reaction product of (i) at least one second dicarboxylic acid and (ii) at least one second monofunctional alcohol, wherein the replacement is substantially free of silicone.

Also described is a personal care formulation that is substantially free of silicone, wherein the formulation comprises a silicone replacement consisting substantially of a mixture of at least one polymeric ester as described above, and a non-polymeric ester as described above. Related methods are also described.

BRIEF DESCRIPTION OF THE SEVERAL VIEWS OF THE DRAWINGS

The foregoing summary may be better understood when read in conjunction with the appended drawings. For the purpose of illustrating aspects of the invention, there is shown in the drawings data and embodiments of the invention. It should be understood, however, that the invention is not limited to the precise arrangements and instrumentalities shown. In the drawings:

FIG. 4 is a table showing the reactant amounts of various sample and comparative sample formulations provided to human test subjects in a panel evaluation of comparative skin feel properties;

FIG. 5 is a copy of the survey used by the panel in evaluating the sample and comparative sample formulations;

DETAILED DESCRIPTION OF THE INVENTION

Figure 1:
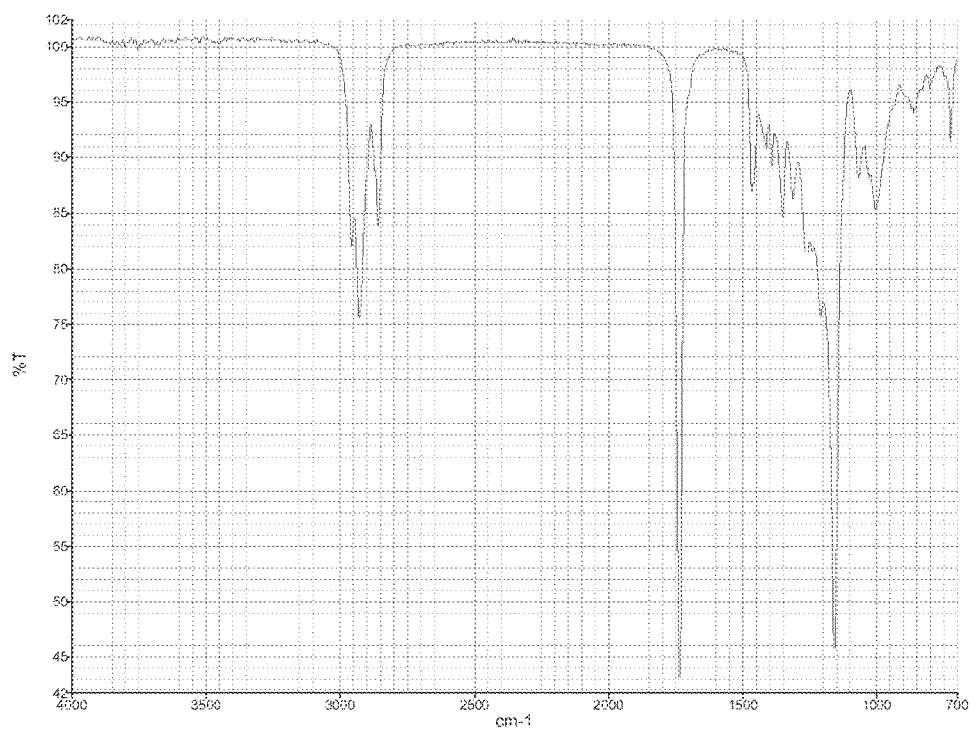
FIG. 1 shows the infrared spectrum of an exemplary non-polymeric ester of the invention, deheptyl succinate.

The invention described herein encompasses silicone replacements for use in personal care formulations (such as, without limitation, shampoos, cleansers, conditioners, cosmetics and lotions) that are substantially free of silicone(s) but have substantially equivalent tactile and/or end use characteristics. Specifically, the applicants have made the surprising discovery that by mixing certain types of natural (i.e., non-petrochemically-derived) ester fluids, certain desirable characteristics ordinarily imparted to personal care formulations by silicone fluids can be realized, including, for example, spreading rate, skin feel, tack reduction, pigment dispersancy, and hair shine. Using the silicone replacements of the invention, one can formulate personal care formulations, including skin and hair products, that contain natural ingredients, are substantially free of silicone, and are perceived by the human end users as having the same or similar aesthetic, tactile and/or skinfeel properties of conventional silicone containing formulations.

By "substantially free of silicone," it is meant that the personal care formulations are formulated without the inclusion of any initial compounds containing silicone groups. For example, the formulations of the invention contain less than 0.09 wt % of silicone, and preferably 0.08% by weight or less.

The invention includes a natural silicone replacement for use in personal care formulations that is a mixture of at least one polymeric ester and at least one non-polymeric ester. The term "natural," as used herein describing any acids, alcohols and/or esters, means that all atoms contained in the structure(s) of the acid, ester or alcohol that are used to prepare the esters are obtained from renewable and/or sustainable sources. By "renewable and sustainable," it is meant that the carbon is not obtained from petrochemical sources. Exemplary carbon sources that are not petrochemical may include, but are not limited to, plant, agricultural or forestry waste biomass.

Particularly useful in the invention are mixtures or blends of non-polymeric and polymeric esters derived from the esterification of natural acids and alcohols. The term "esterification" is used herein to describe a condensation reaction between a carboxylic acid group and/or a carboxylic acid ester group with an hydroxyl group. An "esterification reaction product" is a resultant product of this event. The silicone replacements included in the invention are a blend of polymeric and non-polymeric esters formed from esterification reactions.

Each of the esters present in the silicone replacement fluid is derived from the esterification of at least one dicarboxylic acid. In the practice of the invention, the polymeric ester is an esterification reaction product of at least one first dicarboxylic acid, at least one first monofunctional alcohol or monofunctional carboxylic acid and glycerin and/or a derivative thereof. The polymeric esters in a given silicone replacement may be made from the same first dicarboxylic acid, first monofunctional alcohol or monofunctional carboxylic acid, and glycerin or glycerin derivative or it may be prepared from a mixture of first dicarboxylic acids, first monofunctional alcohols and/or monofunctional carboxylic acids, and glycerin or glycerin derivatives or any permutation of these materials, such that the "polymeric ester" included in the blend/silicone replacement is itself a blend or mixture of various polymeric esters.

The non-polymeric ester of the silicone replacement is a reaction product of at least one second dicarboxylic acid and at least one second monofunctional alcohol. As with the polymeric esters, the non-polymeric ester in a given silicone replacement may be made from the same second dicarboxylic acid and a second monofunctional alcohol or it may be prepared from a mixture of second dicarboxylic acids and second monofunctional alcohols or any permutation of these materials, such that the "non-polymeric ester" included in the blend/silicone replacement is itself a blend or mixture of various non-polymeric esters.

In the case of each of the polymeric ester and the non-polymeric ester, suitable dicarboxylic acids and/or monofunctional alcohols may independently contain carbon chains of medium or short lengths (although the polymeric and non-polymeric esters need not be prepared from initial materials having the same number of carbon atoms). By "short" chain length, it is meant that the compound contains about one to about six carbon atoms. By "medium" chain length, it is meant that the compound contains about seven to about twelve carbon atoms.

In some embodiments, the dicarboxylic acids and/or monofunctional alcohols may independently contain chains of about 1, about 2, about 3, about 4, about 5, about 6, about 7, about 8, about 9, about 10, about 11, about 12, about 13, about 14, or about 15 carbon atoms. In other embodiments, the dicarboxylic acids and/or monofunctional alcohols may independently contain chains of about 10 to about 25 carbon atoms and/or about 1 to about 10 carbon atoms. In any of the embodiments of the invention, one or more of the dicarboxylic acids and/or monofunctional alcohols may independently have carbon chains that are independently linear and/or branched and/or carbon atoms that are independently saturated and/or unsaturated and/or functionalized or unfunctionalized. In some embodiments, at least one of the carbon atoms of the chain is saturated and the others are unsaturated.

Particularly useful acids and/or alcohols may be those that contain linear, saturated chains containing about three to about ten carbon atoms.

Any dicarboxylic acids known or developed in the art may be independently selected for use in the esterification reactions, including, without limitation, 1,4-butanedioic acid (succinic acid), 1,5-pentanedioic acid (glutaric acid), 1,6-hexanedioic acid (adipic acid), 9-nonanedioic acid (azelaic acid) and 1,10-decanedioic acid. In some circumstances, sebacic acid may be preferred.

Any monofunctional dicarboxylic acids known or developed in the art may be independently selected for use in the esterification reaction, including, without limitation hexanoic acid (caproic acid), heptanoic acid, octanoic acid (caprylic acid) nonanoic acid, decanoic acid (capric acid), and dodecanoic acid (lauric acid.) It some circumstances, caprylic acid and capric acid may be preferred.

Glycerin or glycerin derivatives are used in the preparation of the polymeric ester. Glycerin derivatives include, but are not limited to, those derived from the condensation of glycerol with itself to higher glycerol ether derivatives, known as polyglycols.

Any monofunctional alcohols known or developed in the art may be used, including, without limitation 1-hexanol, 1-heptanol, 1-octanol, 2-octanol, and 1-decanol. Under some conditions, 1-heptanol may be preferred.

In each case, it may be preferred that the acid(s), alcohol(s) and/or polyols (glycerin or is derivatives) are natural as defined above.

In the formation of the esters that make up the silicone replacements included in the invention from natural reactants, one or more dicarboxylic acids are esterified with one or more monofunctional alcohols and/or one or more monofunctional carboxylic acid. The esters may be formed by any esterification technique known in the art. For example, in a first reaction, a non-polymeric ester derived from the esterification of one or more monofunctional alcohols with one or more dicarboxylic acids is prepared. In a second reaction, a polymeric ester derived from one or more dicarboxylic acids, one or more monofunctional carboxylic acids, and glycerol and/or polyglycerol is prepared.

To prepare the silicone replacement, non-polymeric and polymeric esters are then blended in an identified ratio such that the replacement imparts to a personal care formulation performance characteristics that correspond the silicone fluid that the mixture is intended to replace, such as a cyclomethicone and/or dimethicone fluids. "Performance characteristics" means the desirable end properties experienced by the consumer and/or the product formulator that silicone fluids impart to personal care formulations, such as spread rate, skin feel and other tactile properties (slip or drag, feeling of oiliness, residual afterfeel, absorption rate into skin, gloss/shine of hair, light- versus heavy-feeling), tackiness (stickiness), and the ability to disperse pigments.

The polymeric and non-polymeric esters may be present in the silicone replacement in any ratio desired, so long as the performance characteristics are achieved or retained. Evaluation of a given blend to ensure it demonstrates adequate and desired performance characteristics as a silicone replacement (as dictated by the end personal care formulation) is a matter of routine testing, well within the skill of an ordinary formulator. In some cases the ratio by weight of polymeric ester to non-polymeric ester may be about 1 to about 1 to about 1:to about 50 (that is, ~1:~1 to ~1:~50).

In some circumstances, as a matter of formulation convenience, it may be desirable to use an identified ratio of polymeric polymer to non-polymeric polymer in the silicone replacement that is adjusted so that the silicone replacement has a specific viscosity. (That way, a personal care product formulator seeking to substitute a silicone replacement into his/her formulation in place of a silicone of a specific viscosity will not have to modify his/her formulation in other ways, increasing the convenience of the silicone replacement.) In such circumstances, the indentified ratio may determined by measuring the viscosity of the end product (the silicone replacement), and adjusting the ratio as necessary to arrive at the target viscosity. For example, one may desire a silicone replacement that has a viscosity of about 1 to about 1000 cSt, about 10 to about 500 cSt, about 20 to about 350 cSt, about 50 to about 200 cSt and/or about 70 to about 100 cSt. In some circumstances, for ease of handling by personal care formulators, it may be desirable to prepare silicone replacements having an identified ratio of polymeric to non-polymeric esters that results in viscosities of about 10, about 20, about 50, about 100, about 200, and/or about 350 (all cSt).

The invention also includes personal care formulations that are natural and are substantially free of silicone. The personal care formulations include the silicone replacement of the invention and at least one more ingredient (that is not a silicone). Any ingredient that can be applied to hair, skin or nails may be included, including pharmacological agents. Exemplary ingredients may include, without limitation, a surfactant, a flavorant, a fragrance, an opacifier, a colorant, a wax, an emulsifier, a fat, an oil, a preservative, a UV absorbing compound, a detergent, foaming agents, stabilizers, pH modifiers, foaming agents, moisturizers, water, an alcohol, a urea, a cosmetic active, a pigment, a wetting agent, a skin or hair conditioner and a solvent. Others may include acetone, water, alcohol, parabens, mineral oil, vegetable oil, olive oil, paraffin, PEG, polyethylene, polyethylene glycol, polyoxyethylene, oxynol, petrolatum, sodium lauryl sulfate, sodium laureth sulfate, sodium myreth sulfate, sodium oleth sulfate, sodium ceteareth sulfate, DMDM hydantoin, sodium hydroxymethylglycinate, triethanolamine, cocamide diethanolamine, laurimide diethanolamine, linoleamide diethanolamine, oleamide diethanolamine, oxybenzone, essential oils, an emollient, octylmethoxycinnamate, titanium dioxide, and zinc oxide.

The personal care formulation may be prepared by any means known in the art and the methods will necessary vary depending on the specific type of personal care formulation being prepared (e.g., underarm antiperspirant formulation versus a skin cleanser formulation). The personal care formation itself make take the form of a solid, semi-solid, liquid, gel, aerosolized or aerosolizable material, film, paste, cream, lotions, emulsion, suspension, and/or powder.

The silicone replacement may be present in the personal care formulation in any amount; the amount will vary depending on a variety of factors, including specific type of personal care formulation being prepared. In may circumstances it may be preferred that the silicone replacement is present in the personal care formulation in an amount of about 1% to about 95% by weight, about 5% to about 80% by weight, about 10% to about 70% by weight, about 15% to about 60% by weight, about 20% to about 50% by weight, or about 30% to about 40% by weight of the total composition. It may be preferred that the silicone replacement is present in the amount of about 1%, about 2%, about 3%, about 4%, about 5%, about 6%, about 7%, about 8%, about 9% by weight of the total composition.

Both the silicone replacements and personal care formulations included in the invention as described herein exhibit similar or the same end properties as compared to their convention silicone containing counterparts. In particular, the difference between a spread value of either a silicone blend of the invention or of a personal care formulation of the invention ("invention spread value") and a spread value of a corresponding conventional silicone or conventional silicone containing personal care formulation ("conventional spread value") is less than about 10%, less than about 5%, less than about 1% of the total conventional spread value. Additionally, the skinfeel properties, the tackiness (stickiness) and the pigment dispersion capabilities of the silicone replacements and that of the convention silicone containing counterpart are similar or statistically identical.

Example 1

Preparation of an Exemplary Non-Polymeric Ester of the Invention

The reaction product of 1-heptanol and succinic acid ("diheptyl succinate") was prepared. To a five liter four neck flask equipped with a stirrer, heating mantle, nitrogen gas sparge, vapor column, and total condenser, 2813 grams (24.25 gram moles) of n-heptanol were added. 938 grams (7.94 gram moles) of succinic acid were added. To this, 7.5 grams of ethanesulfonic acid (70% aqueous solution) was added as a catalyst.

The mixture was heated to about 150° C., and vacuum was slowly staged in. At the completion of this step, the acid value of the material was measured to be 0.90 mg KOG/g. The mixture was then cooled to about 90° C. and a solution of sodium carbonate was added to neutralize the residual acidity.

The ester was then batch distilled followed by steam stripping. The stripped ester was treated with activated charcoal, and filtered yielding an essentially odorless and colorless fluid.

Analytical properties of the ester are shown below in Table 1.

TABLE 1

| Property | Units | Result |
| --- | --- | --- |
| Color | APHA | 23 |
| Acid Value | mg KOH/g | 0.035 |
| Hydroxyl Value | mg KOH/g | 0.25 |
| Odor | Organoleptic | Mild |
| Viscosity at 25° C. | cSt | 8.6 |
| Viscosity at 40° C. | cSt | 5.8 |
| Sp. Gr. 25/25 | — | 0.9338 |
| Flash Point | ° C. | 186 |
| Moisture | % wt/wt | 0.01 |

FIG. 1 shows the infrared spectrum of the non-polymeric ester prepared as described above.

Example 2

Preparation of Exemplary Polymeric Esters of the Invention

Variants of the reaction product of decanedioic acid ("sebacic acid," derived from 5 castor oil) 1,2,3-propanetriol ("glycerol," derived from coconut oil) and octanoic acid ("caprylic acid," derived from coconut oil) were prepared. Reactant amounts for each variant are given in Table 2.1, below.

The esterification/polyesterifications were carried out in a four neck flask equipped with a stirrer, heating mantle, nitrogen gas sparge, vapor column, and total condenser. In each case, the reactants were charged to the vessel and heated to about 215° C.

Pressure was then reduced to drive off the water of reaction and the acid value was monitored to follow the course of the reaction. When the reaction was sufficiently complete (acid value of 5 or lower mg KOH/g), the reactor contents were cooled to about 180° C. and were steam stripped under hard vacuum 15 for about four hours. Steam stripping was stopped, and the reaction product was cooled and discharged into containers. Table 2.2 shows the properties obtained.

Figure 2:
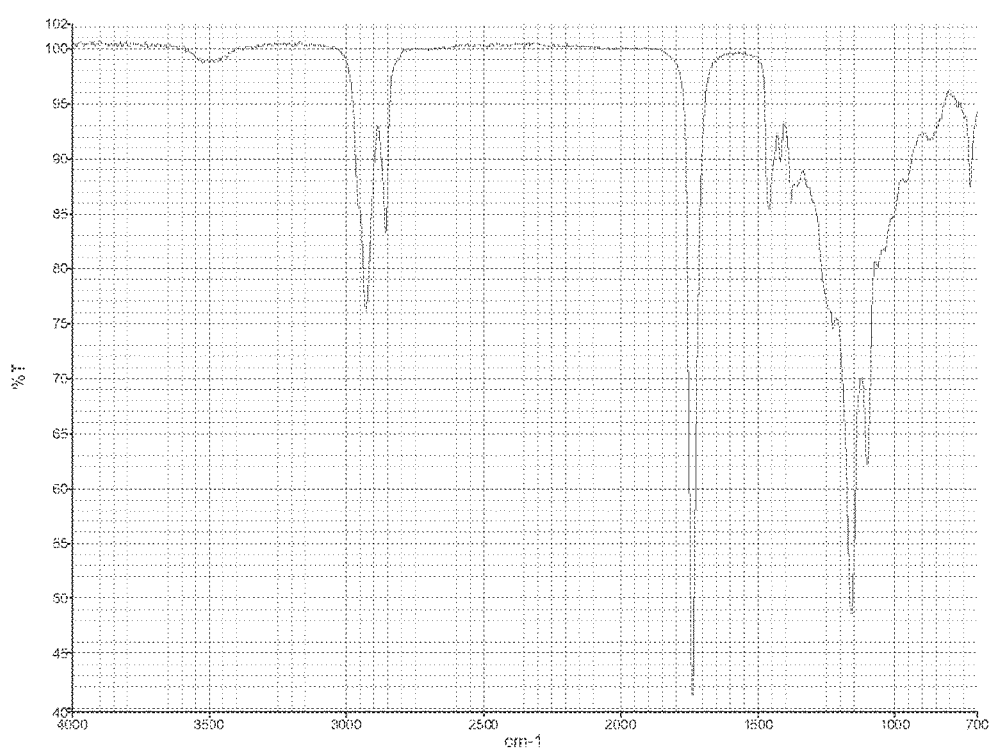
FIG. 2 shows that infrared spectrum of an exemplary polymeric ester of the invention, GSC Type 4.

FIG. 2 shows the infrared spectrum of the exemplary polymeric ester GSC Type

TABLE 2.1

| Product | Octanoic Acid (grams) | Glycerol (grams) | Sebacic Acid (grams) |
| --- | --- | --- | --- |
| GSC Type 1 | 1440 | 960 | 1600 |
| GSC Type 2 | 1462 | 769 | 1269 |
| GSC Type 3 | 1416 | 786 | 1298 |

TABLE 2.1-continued

| Product | Octanoic Acid (grams) | Glycerol (grams) | Sebacic Acid (grams) |
|---|---|---|---|
| GSC Type 4 | 1392 | 774 | 1334 |
| GSC Type 5 | 1558 | 733 | 1209 |
| GSC Type 6 | 1492 | 737 | 1271 |

TABLE 2.2

| Product | Acid Value (mg KOH/g) | Hydroxyl Value (mg KOH/g) | Color (APHA) | Moisture (% wt./wt.) | Viscosity (cP at 25° C.) |
|---|---|---|---|---|---|
| GSC Type 1 | 0.13 | 85.3 | 58 | 0.05 | 5,900 |
| GSC Type 2 | 0.26 | 45.4 | 309 | 0.025 | 3,185 |
| GSC Type 3 | 0.25 | ND | ND | ND | Gelled |
| GSC Type 4 | 0.33 | 49.2 | 120 | 0.011 | 6,200 |
| GSC Type 5 | 0.91 | 26.1 | 188 | 0.026 | 2,525 |
| GSC Type 6 | 1.07 | 26.4 | 327 | 0.005 | 5,100 |

Example 3

Preparation of Exemplary Silicone Replacement of the Invention

The esters of Examples 1 and 2 were blended to make a total of about 1000 grams of test blend by mixing in a glass beaker of suitable size with mechanical stirrer until a clear, homogeneous solution was obtained. Six test blends were prepared (N10, N20, N50, N100, N200, N350) to have the approximate viscosities of 10 cSt, 20 cSt, 50 cSt, 100 cSt, 200 cSt, and 350 cSt, respectively, as measured at 25° C.

Table 3.1 shows the properties obtained for exemplary silicone replacement of the invention.

TABLE 3.1

| Blend ID | GSC Type 4 (wt. %) | DHS (wt. %) | Viscosity at 25° C. (cSt) | Flash Point (° C.) | Refractive Index | Sp.G.r. 25/25 |
|---|---|---|---|---|---|---|
| N10 | 2.0 | 98.0 | 10.0 | 195 | 1.4395 | 0.9356 |
| N20 | 11.3 | 88.7 | 19.7 | 198 | 1.4417 | 0.9443 |
| N50 | 27.5 | 72.5 | 53.8 | 206 | 1.4456 | 0.584 |
| N100 | 32.5 | 67.5 | 109 | 200 | 1.4480 | 0.9691 |
| N200 | 44.0 | 56.0 | 206 | 208 | 1.4507 | 0.9798 |
| N350 | 52.5 | 47.5 | 351 | 204 | 1.4529 | 0.9892 |

Example 4

Evaluation of Spread Rate of Silicone Replacement

An evaluation of the spread rates of the silicones replacements included in the invention as compared to the spread rate of various dimethicones commonly used in personal care formulations was carried out. As is understood in the art, the rate of spreading or spreading value is indicative of the ability of the formulation to flow over the skin upon application, and is regarded as a significant measurement in determining the attributes of a final personal care formulation.

Figure 3:
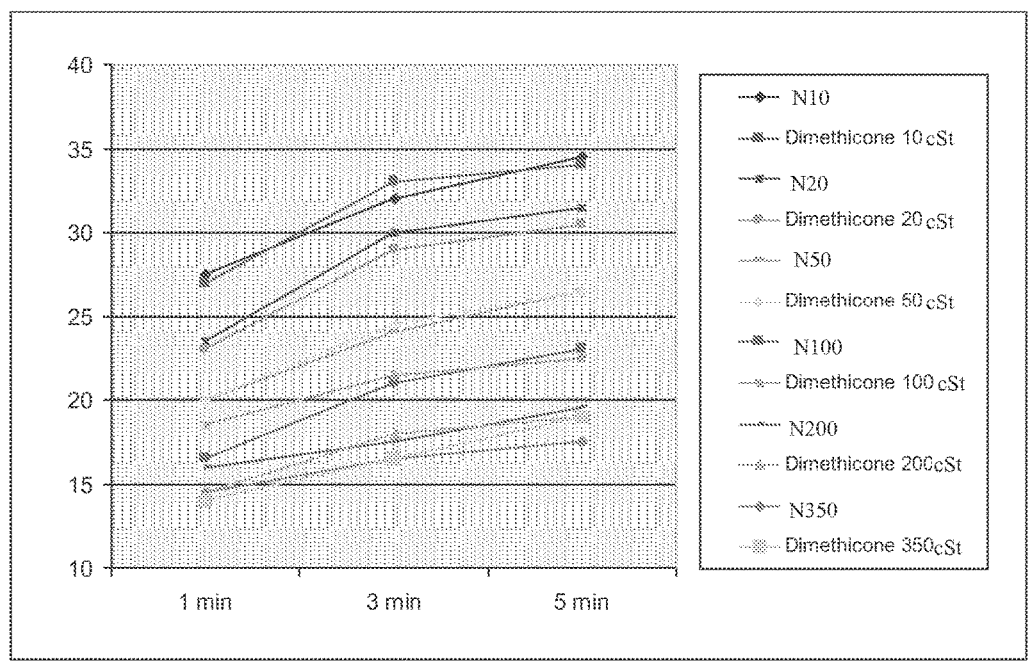
FIG. 3 shows spread rate of the silicone replacement as compared to that of the conventional silicone material in graphic form.
Figure 6A:
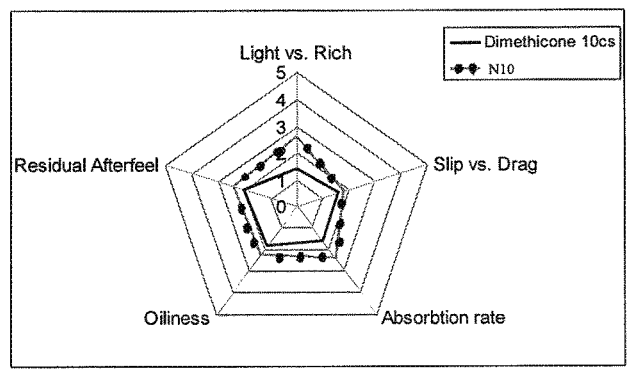
FIG. 6A is a chart presenting the skinfeel data collected from a panel of evaluators who compared the skinfeel of an embodiment of the invention to that of a control formulation containing a dimethicone.
Figure 6B:
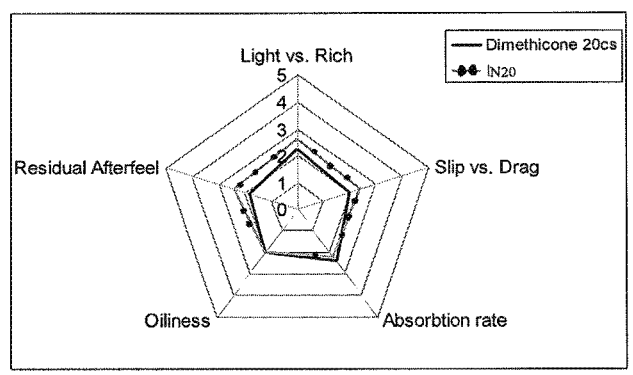
FIG. 6B is a chart presenting the skinfeel data collected from a panel of evaluators who compared the skinfeel of a first additional embodiment of the invention to that of a control formulation containing a dimethicone.
Figure 6C:
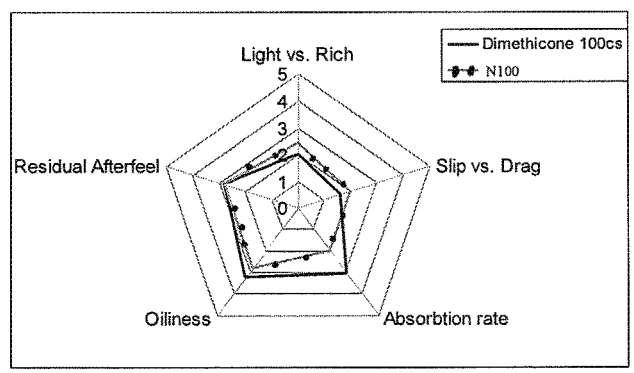
FIG. 6C is a chart presenting the skinfeel data collected from a panel of evaluators who compared the skinfeel of a second additional embodiment of the invention to that of a control formulation containing a dimethicone.
Figure 6D:
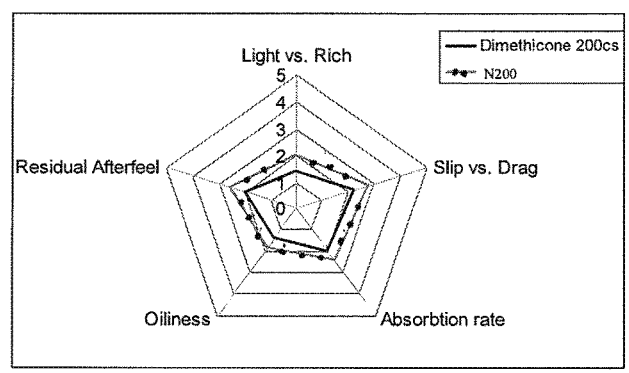
FIG. 6D is a chart presenting the skinfeel data collected from a panel of evaluators who compared the skinfeel of a third additional embodiment of the invention to that of a control formulation containing a dimethicone.
Figure 6E:
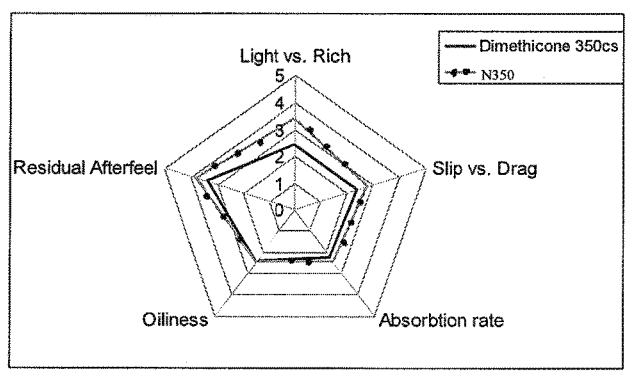
FIG. 6E is a chart presenting the skinfeel data collected from a panel of evaluators who compared the skinfeel of a fourth additional embodiment of the invention to that of a control formulation containing a dimethicone.
Figure 7A:
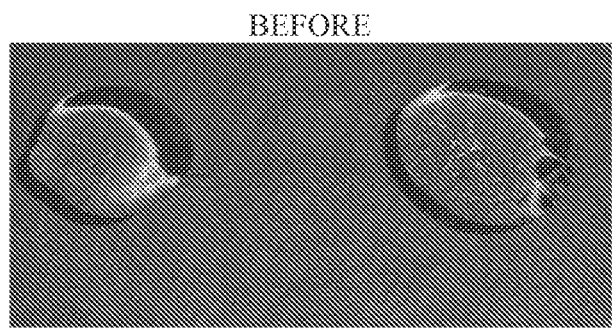
FIG. 7A shows a control formulation sample and a sample that is an embodiment of the invention before evaluation by the cotton ball tackiness test.
Figure 7B:
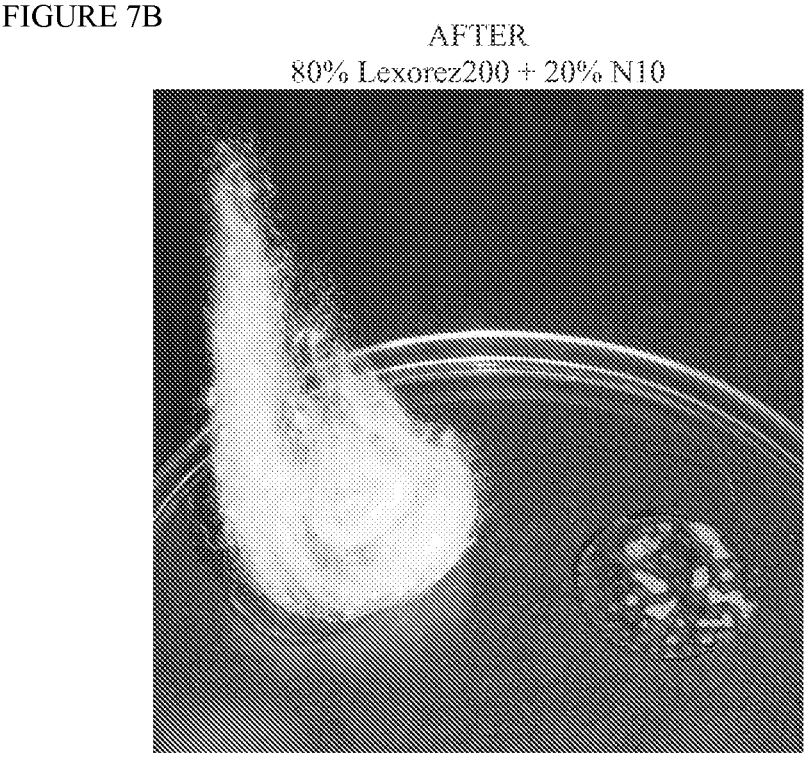
FIG. 7B shows the samples of FIG. 7A after evaluation by the cotton ball tackiness test.
Figure 7C:
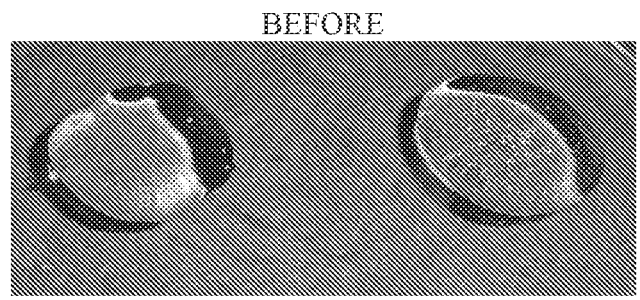
FIG. 7C shows a control formulation sample and a sample that is a first additional embodiment of the invention before evaluation by the cotton ball tackiness test.
Figure 7D:
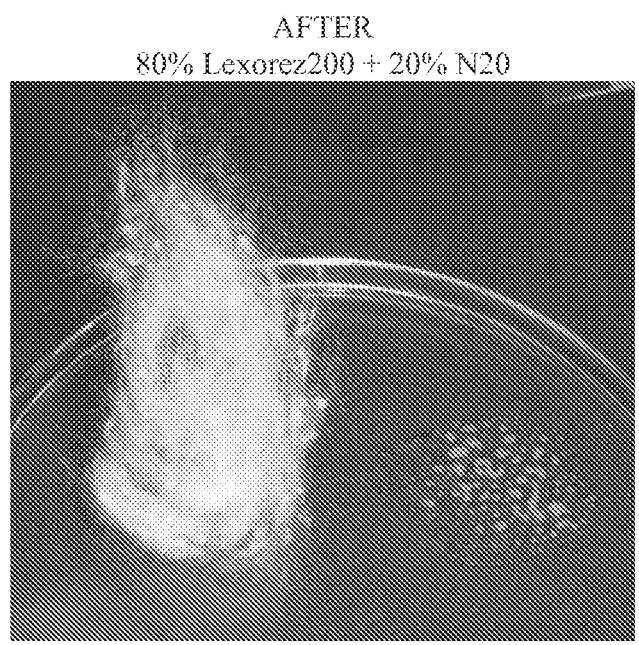
FIG. 7D shows the samples of FIG. 7C after evaluation by the cotton ball tackiness test.
Figure 7E:
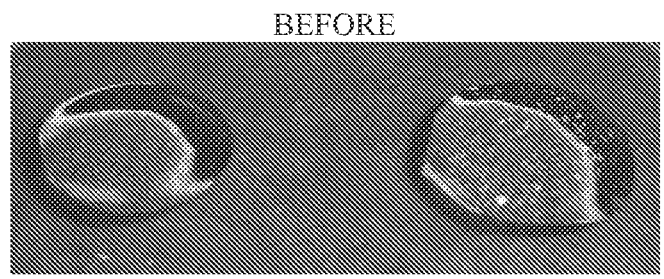
FIG. 7E shows a control formulation sample and a sample that is a second additional embodiment of the invention before evaluation by the cotton ball tackiness test.
Figure 7F:
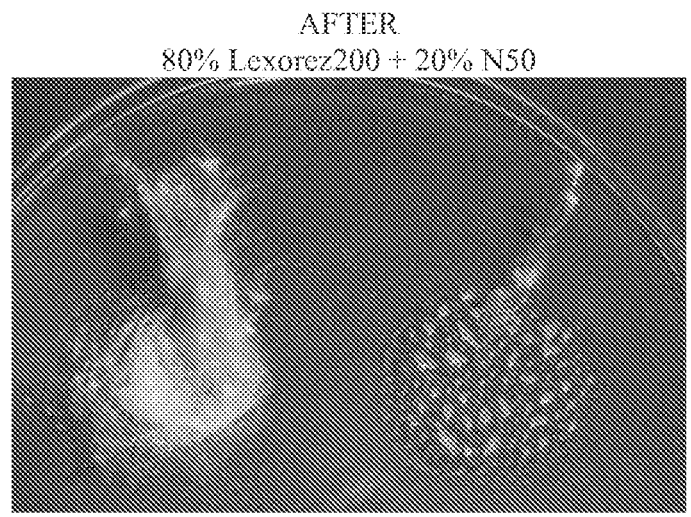
FIG. 7F shows the samples of FIG. 7E after evaluation by the cotton ball tackiness test.
Figure 7G:
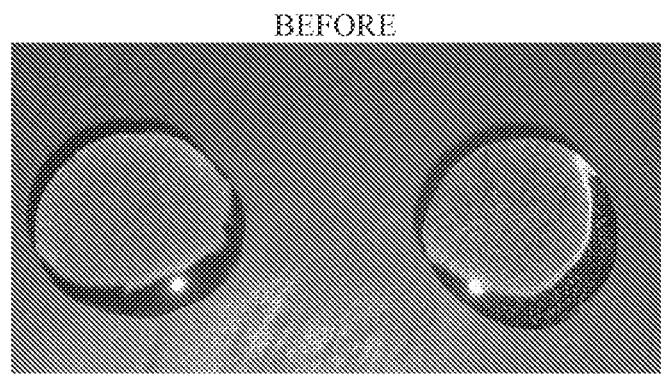
FIG. 7G shows a control formulation sample and a sample that is a third additional embodiment of the invention before evaluation by the cotton ball tackiness test.
Figure 7H:
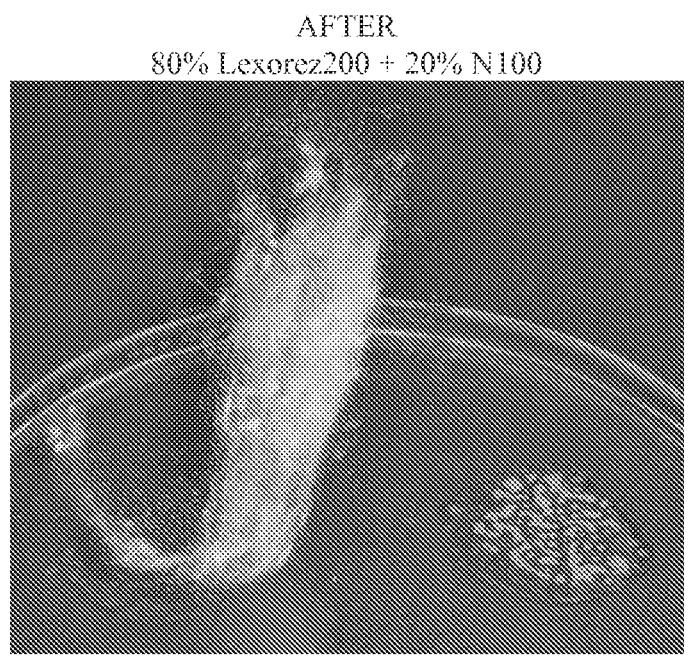
FIG. 7H shows the samples of FIG. 7G after evaluation by the cotton ball tackiness test.
Figure 7I:
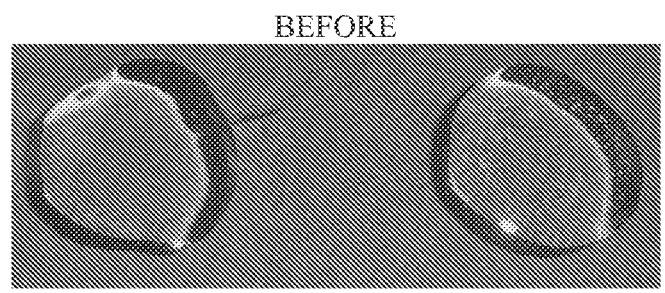
FIG. 7I shows a control formulation sample and a sample that is a fourth additional embodiment of the invention before evaluation by the cotton ball tackiness test.
Figure 7J:
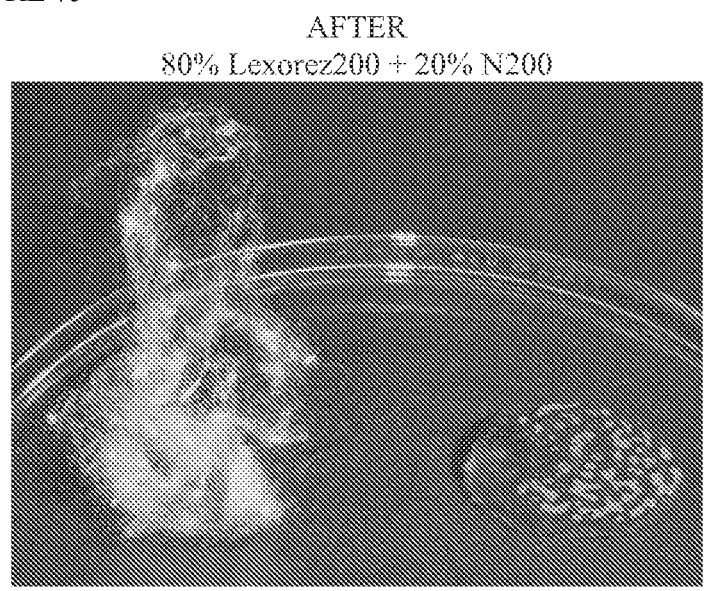
FIG. 7J shows the samples of FIG. 7I after evaluation by the cotton ball tackiness test.
Figure 7K:
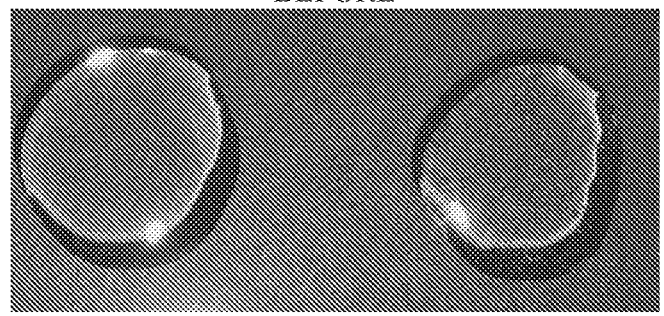
FIG. 7K shows a control formulation sample and a sample that is a fifth additional embodiment of the invention before evaluation by the cotton ball tackiness test.
Figure 7L:
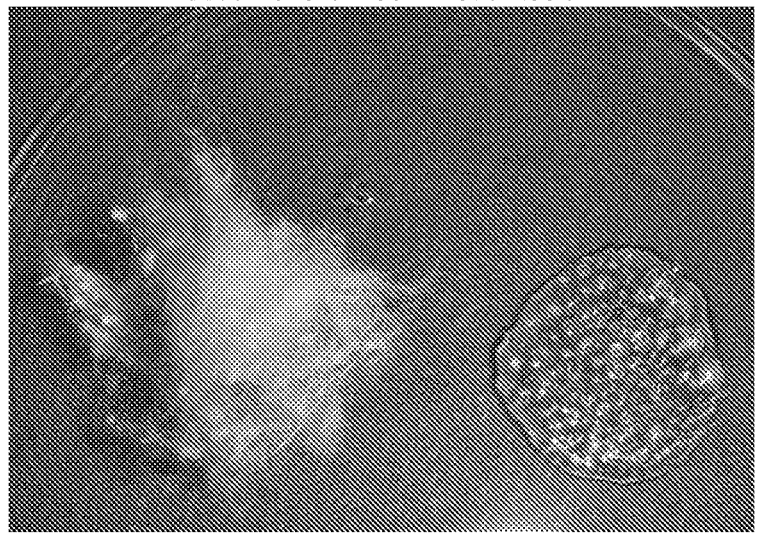
FIG. 7L shows the samples of FIG. 7K after evaluation by the cotton ball tackiness test.

Six samples of the silicone replacement of the invention (S1-S6) prepared in example 3 and six comparative samples of dimethicone fluid (CS1-CS6) were evaluated, each of varying viscosity, as shown in the table below:
Samples Blend ID Comparative
Samples
S1 N10 CS1 Dimethicone 10 cst
S2 N20 CS2 Dimethicone 20 cst
S3 N50 CS3 Dimethicone 50 cst
S4 N100 CS4 Dimethicone 100 cst
S5 N200 CS5 Dimethicone 200 cst
S6 N350 CS6 Dimethicone 350 cst Samples S1-S6 (Blend IDS N10, N20, N50, N100, N200, N350) were prepared using the method set forth in Example 3. Each sample S1-S6 and CS1-CS6 was handled as follows: A piece of filter paper was placed over a Petri dish. Using a pipeter, 50 L of the sample was applied to the approximate center of the filter paper. After the lapse of each of 1 minute, 3 minutes and 5 minutes, the circumference of the sample was traced onto the paper. The diameter of each of the circles created was measured. Two measurements were taken for each sample at each time interval. The measurements are shown below. As plotted, the measurements are shown in FIG. 3, by viscosity.

FIG. 3

| Samples | Blend ID | Comparative Samples |
|---|---|---|
| S1 | N10 | CS1 Dimethicone 10 cst |
| S2 | N20 | CS2 Dimethicone 20 cst |
| S3 | N50 | CS3 Dimethicone 50 cst |
| S4 | N100 | CS4 Dimethicone 100 cst |
| S5 | N200 | CS5 Dimethicone 200 cst |
| S6 | N350 | CS6 Dimethicone 350 cst |

Example 5

Comparison of Skin Feel Properties Between Mixtures of the Invention and Silicone Fluids Samples were prepared as follows, using the reactant amounts as shown in the table of FIG. 4. Water in the amount shown for phase A was heated to 78-80 C. Using a propeller, the remainder of phase A ingredients were combined together into a slurry, then mixed into the heated water. The combined phase "B" ingredients were heated to 80 C and added to the phase "A" with continued mixing. The entire mixture was allowed to cool to 60 C. Phase "C" was added to each batch and the entire mixture was cooled to room temperature.

Four ounces of each formulation was packaged in a glass jar. Study participants were directed to apply 0.10-0.20 g of lotion to hid or her inner forearm (one formulation to 15 each arm). Participants were then asked to complete a survey. The survey is attached hereto as FIG. 5. Data generated from the surveys are plotted in FIG. 6A to 6D.

The results of this study indicate that the silicone replacements perform similar to the dimethicone counterparts.

Six sample blends (S1-S6) were created by combining 20% by weight of Lexorex 200 (a proprietary blend of trimethylpentanediol/adipic acid/glycerine crosspolymer; available from Inolex Chemical Company, Philadelphia, Pa. USA) and 80% by weight of each of the samples S1-S6, as shown below:

| Sample No. | Sample Blend ID |
|---|---|
| S1 | N10 |
| S2 | N20 |
| S3 | N50 |
| S4 | N100 |
| S5 | N200 |
| S6 | N350 |

Lexorez 200 is a viscous polyester having a viscosity of approximately 25,000 cP at 25° C. Samples S1-S6 were prepared as set out in Example 3. Using a disposable transfer pipet, 0.20 g of Lexorez 200 was applied to the left side of a Petri dish and 0.20 g of each of S1-S6 was applied to the right side of the dish. Each sample was manually spread to cover a circle having a diameter of 2 centimeters. A standard cotton ball (purchased from a beauty supply store) was placed over each sample circle. The cotton ball was pressed into the sample, and then pulled away using an upward motion. The amount of cotton fiber remaining on each sample circle was visually assessed and recorded by photographic means.

The photos created are shown in FIG. 7. In each case, the silicone replacements of the invention exhibit decreased or low tackiness (dry skin feel), a characteristic associated with silicones.

Example 6

Evaluation of Pigment Grind

The capability of the silicone replacements to act as pigment dispersant was assessed by evaluation of viscosity and appearance of pigment grinds. This capability is significant, since high concentration, low viscosity pigment dispersions are used in color cosmetics.

Nine test formulations were prepared by combining the ingredients as shown in the table below:

|  | A | B | C | D | E | F | G | H | I |
|---|---|---|---|---|---|---|---|---|---|
| N10 | 50.00 | | | | | | | | |
| N20 | | 50.00 | | | | | | | |
| N50 | | | 50.00 | | | | | | |
| N100 | | | | 50.00 | | | | | |
| N200 | | | | | 50.00 | | | | |
| N350 | | | | | | 50.00 | | | |
| Dimenthicone 50 cst | | | | | | | 50.00 | | |
| Castor Oil | | | | | | | | 50.00 | |
| LexFeel 700 | | | | | | | | | 50.00 |
| Red 7 Lake | 50.00 | 50.00 | 50.00 | 50.00 | 50.00 | 50.00 | 50.00 | 50.00 | 50.00 |

Figure 8:
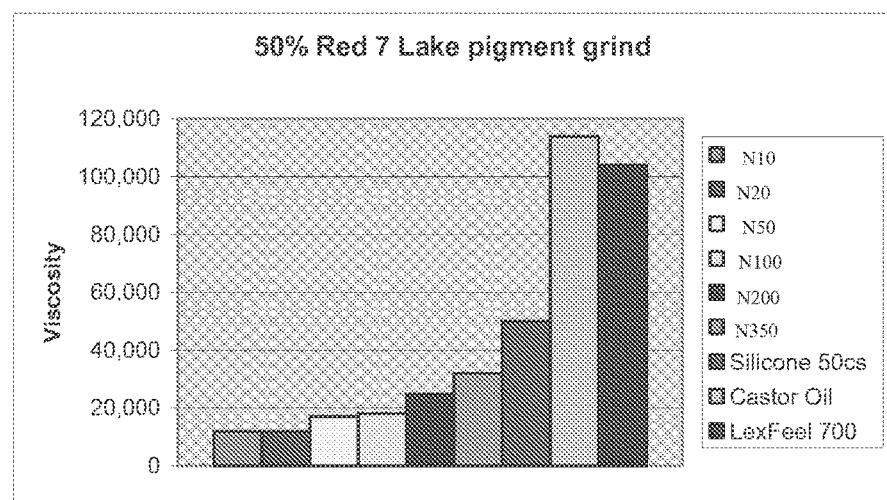
FIG. 8 shows the results of a pigment grind evaluation.

LexFeel 700 is a blend of pentaenthrity/heptanoate/caprylate/caprate available from Inolex Chemical Company, Philadelphia, Pa., USA. Blends N10, N20, N50, N100, N200, N350 were prepared as set out in Example 3. The test selected dimethicone/silicone replacement was mixed slowly with the red lake pigment until pigment is wetted out to avoid losing pigment in a dust cloud. Mixing was continued until the pigment was completely dispersed. The viscosity of each test blend A to I was measured using Brookfield viscometer using spindle T-D and helipath stand. The results are shown in FIG. 8.

The data indicate that the series silicone replacements are comparative to the silicone blend, and facilitate acceptable pigment dispersant. The silicone replacement blends were easy to mix and the resulting viscosities were low.

Example 7

Evaluation of Shine

The ability of the silicone replacements to impart shine as compared to dimethicone counterparts was evaluated, specifically on human hair. Silicones, both dimethicone and cyclomethicone, are routinely used to add shine capabilities to hair styling products, but often build up on hair and do not decompose once washed away into the environment. Test formulations A to L were prepared by mixing the ingredients for each as shown in the table below:

|  | A | B | C | D | E | F | G | H | I | J | K | L |
|---|---|---|---|---|---|---|---|---|---|---|---|---|
| Isododecane | 80 | 80 | 80 | 80 | 80 | 80 | 80 | 80 | 80 | 80 | 80 | 80 |
| N10 | 20 | — | — | — | — | — | — | — | — | — | — | — |
| Dimethicone 10 cst | — | 20 | — | — | — | — | — | — | — | — | — | — |
| N20 | — | — | 20 | — | — | — | — | — | — | — | — | — |
| Dimethicone 20 cst | | | | 20 | | | | | | | | |
| N50 | | | | | 20 | | | | | | | |

-continued

|   | A | B | C | D | E | F | G | H | I | J | K | L |
|---|---|---|---|---|---|---|---|---|---|---|---|---|
| Dimethicone 50 cst | | | | | | | 20 | | | | | |
| N100 | | | | | | | | | | 20 | | |

Blends N10, N20, N50, N100, N200 and N350 where prepared as set forth in Example 3.

Figure 9:
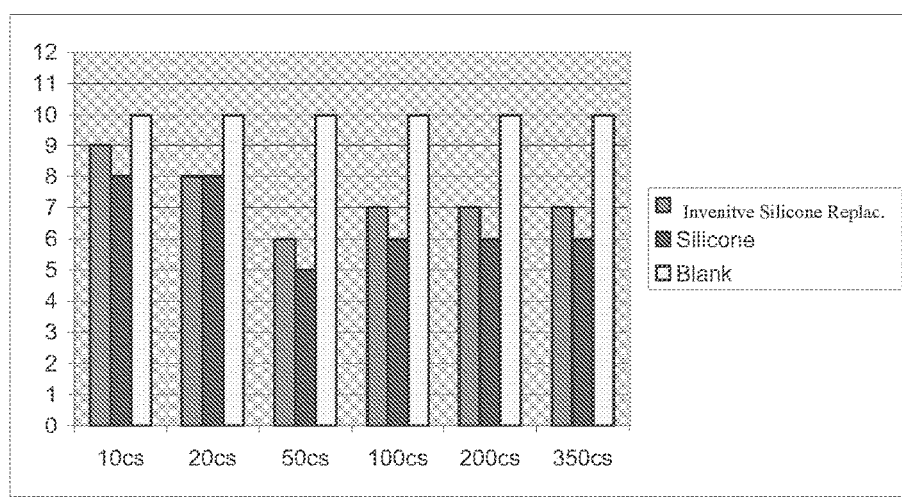
FIG. 9 shows the results of a shine (gloss) evaluation of hair to which the silicone replacements were applied.

Virgin human hair tresses were cut into thirteen strips of 8 cm. Each tress was shampooed and rinsed with deionized water for one minute. Each tress was sprayed with one of the test formulations A to L, with one tress remaining untreated. Each tress was wrapped around a 28 cm cylinder and allowed to air dry. To evaluate shine, the cylinder was place on a flat surface 1 meter away from power-light work light. All other light sources were eliminated. The cylinder with tresses was illuminated with the power light. A photo of the hair was taken and the bandwidth of the shine was measured. The data collected is graphically shown in FIG. 9. Based upon these data, it can be concluded that the silicone replacements are comparable to the dimethicone counterparts as they contribute similar shine to the hair, leaving a high gloss finish.

Example 8

Natural Skin Moisturizing Lotion

A natural skin moisturizing lotion is prepared using the silicone replacement of the invention. The ingredients used in the formulation are set forth in the table below:

| Phase | Ingredient | Amount (wt %) |
|---|---|---|
| A | Water | 70.15 |
| A | Panthenol | 0.1 |
| B | Glycerin | 5.0 |
| B | Microcrystalline cellulose and cellulose gum | 1.0 |
| B | Xanthan gum | 0.2 |
| C | Cetearyl alcohol and cetearyl glucoside | 5.0 |
| C | N100 (Example 3) | 10.0 |
| C | Jojoba esters | 2.0 |
| C | Cetyl alcohol | 2.0 |
| C | *Helianthus annus* oil | 3.0 |
| C | Tocopheryl acetate | 0.1 |
| C | Caprylhydroxamic acid and glyceryl caprylate and glycerin | 1.0 |

The ingredients of phase A are mixed and heated to 80° C. The ingredients of phase C are premixed with one another, then are added to the heated phase A mixture with propeller mixing. The A/C mixture is heated to 80° C. The ingredients of phase B are premixed. Once the A/C mixture is at 80° C., the A/C mixture is added to the phase B premix with propeller mixing. Mixing is continued until the entire formulation is uniformly mixed. The formulation is cooled to room temperature while mixing is maintained.

Upon evaluation, it is determined that the lotion has a pH of 5.82 at 25° C. and a Brookfield viscosity of 39,000 cps at 25° C. and that the lotion has both a dry skin feel and a pigment dispersion capability similar to that to a lotion that contains dimethicone.

Example 9

Antiperspirant Stick

An antiperspirant stick formulation is prepared suing the replacement of the invention. The ingredients used in the preparation are set forth below:

| Phase | Ingredient | Amount (wt %) |
|---|---|---|
| A | N5 (Example 3) | 56.0 |
| A | Hydroxystearic acid | 10.0 |
| B | Talc | 6.0 |
| B | Silica | 4.0 |
| B | Aluminum zirconium tetrachlorohydrex/glycine | 26.0 |

The ingredients of phase A are mixed using moderate propeller agitation and heated to 80° C. Subsequently, each phase B ingredient is added individually to the phase A mixture while temperature is maintained. Mixing is accomplished using moderate propeller agitation. The final mixture is cooled to room temperature.

The resulting antiperspirant product contains no silicones, but exhibits the dry skin feel and smooth application properties of cyclomethicone-containing formulations.

Example 10

Natural Lip Stain

A natural lip stain formulation is prepared suing the replacement of the invention. The ingredients used in the preparation are set forth below:

| Phase | Ingredient | Amount (wt %) |
|---|---|---|
| A | N350 (Example 3) | 37.30 |
| A | N5 (Example 3) | 20.0 |
| A | Distarch Phosphate | 5.0 |
| A | *Argnia Spinosa* (Argan) Kernel Oil | 1.5 |
| A | *Triticum Vulgare* (Wheat) Germ Oil | 3.0 |
| A | *Prunus Armeniaca* (Apricot) Kernel Oil | 2.0 |
| A | *Copernica Cerifera* (Carnauba) Wax | 12.0 |
| A | *Euphorbia Cerifera* (Candelilla) Wax | 4.0 |
| A | *Maqnifera Indica* (Manqo) Seed Butter | 2.0 |
| A | *Butyrosperum Parkii* (Shea) Butter | 1.0 |
| A | Glyceryl Caprylate (and) Glyceryl Undecylenate | 0.8 |
| B | Mica Sericite | 6.0 |
| B | Titanium Dioxide | 2.0 |
| B | Yellow 6 Lake | 0.8 |
| B | Red 6 Lake | 0.2 |
| B | Mica (and) Titanium Dioxide | 1.5 |

-continued

| Phase | Ingredient | Amount (wt %) |
|---|---|---|
| C | Tocopheryl Acetate Vitamin E Acetate | 0.3 |
| C | Retinyl Palmitate Vitamin A Palmitate | 0.3 |
| C | Fragrance | 0.3 |

The ingredients of phase A are combined and heated to about 80° C. to 85° C. while undergoing propeller mixing. The phase B pigments are ground, then added to phase A. The mixture is mixed until it appears visually uniform. The heat is removed, and the ingredients of phase C are added. The final mixture is cooled and packaged.

Upon evaluation it is demonstrated that the formulation has a pH of 5.25 at 25° C. and a Brookfield viscosity of 82,000 cps. Moreover, it is found that the lip stain formulation provides spreadability and skin feel properties like those of dimethicone-containing formulations.

Example 11

Silicone-Free Natural Hair Conditioner

A natural silicone-free hair conditioner is prepared suing the replacement of the invention. The ingredients used in the preparation are set forth below:

| Phase | Ingredient | Amount (wt %) |
|---|---|---|
| A | Water | |
| A | Glycerine | |
| A | Arginine | |
| B | Brassicyl Isoleucinate Esylate (and) *Brassica* Alcohol | |
| B | N350 (Example 3) | 8.0 |
| B | Glyceryl Caprylate (and) Glyceryl Undecylenate | 1.0 |
| B | *Orbignya Speciosa* Kernel Oil (and) *Astrocaryum* Murumuru Seed Butter | 1.0 |

To prepare the conditioner, one combines the ingredients of phase A, and heats them to 75° C. with propeller mixing. Separately, one combines the ingredients of phase A also heating them to 75° C. with propeller mixing. The heat is removed and phase B is added to phase A. When the mixture has cooled to 35° C., the ingredients of phase C are added. The entire formulation is cooled to room temperature while mixing.

Evaluation of the formulation demonstrates that it has a pH of 3.85 at 25° C. and a Brookfield viscosity of 35,000 cps at 25° C. In addition, the conditioner provides a feel and a shine to hair comparable to silicone-containing formulations.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A silicone replacement for use in a personal care formulation comprising a mixture of at least one polymeric ester and at least one non-polymeric ester, wherein the polymeric ester is an esterification reaction product of (i) at least one first dicarboxylic acid, (ii) at least one first monofunctional alcohol or monofunctional carboxylic acid and (iii) glycerin or derivatives thereof; and the non-polymeric ester is an esterification reaction product of (i) at least one second dicarboxylic acid and (ii) at least one second monofunctional alcohol, wherein the replacement is substantially free of silicone.

2. The replacement of claim 1, wherein at least one of the polymeric ester and the nonpolymeric ester is natural.

3. The replacement of claim 1, wherein at least one of the first or the second monofunctional alcohols is independently chosen from monofunctional alcohols having about 1 carbon atom to about 25 carbon atoms.

4. The replacement of claim 1, wherein at least one of the first or the second monofunctional alcohols is independently chosen from monofunctional alcohols having about 1 carbon atom to about 10 carbon atoms.

5. The replacement of claim 1, wherein at least one of the first or the second monofunctional alcohols is independently chosen from a monofunctional alcohol having about 1 carbon atom, a monofunctional alcohol having about 2 carbon atoms, a monofunctional alcohol having about 3 carbon atoms, having about 4 carbon atoms, a monofunctional alcohol having about 5 carbon atoms, having about 6 carbon atoms, a monofunctional alcohol having about 7 carbon atoms, a monofunctional alcohol having about 8 carbons atoms, a monofunctional alcohol having about 9 carbon atoms, a monofunctional alcohol having about 10 carbon atoms, a monofunctional alcohol having about 11 carbon atoms, and a monofunctional alcohol having about 12 carbon atoms.

6. The replacement of claim 1, wherein at least one of the first or the second monofunctional alcohols is independently a linear chain monofunctional alcohol.

7. The replacement of claim 1, wherein at least one of the first or the second monofunctional alcohols contains saturated carbon atoms.

8. The replacement of claim 7, wherein all of the carbon atoms present in the at least one of the first or the second monofunctional alcohols are saturated.

9. The replacement of claim 1, wherein at least one of the first dicarboxylic acid or the second dicarboxylic acid is independently chosen from dicarboxylic acids having about 15 carbon atom to about 25 carbon atoms.

10. The replacement of claim 1, wherein at least one of the first dicarboxylic acid or the second dicarboxylic acid is independently chosen from dicarboxylic acids having about 5 carbon atoms to about 10 carbon atoms.

11. The replacement of claim 1, wherein the replacement exhibits a spread rate that is substantially equivalent to a spread rate of a counterpart silicone fluid.

12. The replacement of claim 1, wherein the replacement exhibits a pigment dispersion capability that is substantially equivalent to pigment dispersion capability of a counterpart silicone fluid.

13. The replacement of claim 1, wherein the replacement exhibits skinfeel properties that are substantially equivalent to skinfeel properties of a counterpart silicone fluid.

14. The replacement of claim 1, wherein the replacement exhibits a tack (stickiness) that is substantially equivalent to a tack (stickiness) of a counterpart silicone fluid.

* * * * *